US006355008B1

(12) United States Patent
Nakao

(10) Patent No.: US 6,355,008 B1
(45) **Date of Patent: *Mar. 12, 2002**

(54) COMPRESSED AIR-DISTRIBUTING DEVICE AND VALVE FOR USE IN THE DEVICE

(75) Inventor: Haruki Nakao, Tokyo (JP)

(73) Assignee: Nitto Kohki Co., Ltd., Tokyo (JP)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/103,934

(22) Filed: Jun. 25, 1998

(30) Foreign Application Priority Data

Jul. 1, 1997 (JP) ............................................ 9-188967

(51) Int. Cl.[7] ................................................ A61M 7/00

(52) U.S. Cl. ........................ 601/150; 601/149; 601/152

(58) Field of Search ................................ 601/148, 149, 601/150, 151, 152

(56) References Cited

U.S. PATENT DOCUMENTS 2,533,504 A 12/1950 Poor
3,583,426 A * 6/1971 Feres ......................... 137/240
4,577,626 A * 3/1986 Marukawa et al. ......... 601/150
4,825,486 A 5/1989 Kimura et al.
5,598,872 A * 2/1997 Kasugai et al. ............. 137/854

FOREIGN PATENT DOCUMENTS

JP 51-23127 8/1949
JP 07171184 7/1995
JP 07171185 7/1995

* cited by examiner

*Primary Examiner*—Michael A. Brown
*Assistant Examiner*—Benjamin U. Koo
(74) *Attorney, Agent, or Firm*—Fulbright & Jaworski, L.L.P.

(57) ABSTRACT

A device for distributing compressed air from a compressed air source to a plurality of apparatus that use compressed air. The device comprises a housing having valve chambers, inlet ports for connecting the valve chambers to the compressed air source, outlet ports, and exhaust ports communicating with outside the device. Each outlet port is adapted to communicate with at least one of the apparatus that use compressed air. Spherical valve bodies movably are provided in the valve chambers, respectively, each for closing one inlet port and one exhaust port. Shafts extend from the valve bodies, respectively. Each shaft has an end portion passing through one exhaust port and protruding from the housing. Electromagnetic actuators are coupled to the end portions of the shafts, respectively. Each actuator moves one valve body between an air supplying position where the valve body closes the exhaust port and connecting the inlet port and the outlet port, and an air-exhausting position where the valve body closes the inlet port and connecting the outlet port and the exhaust port.

7 Claims, 2 Drawing Sheets

COMPRESSED AIR-DISTRIBUTING DEVICE AND VALVE FOR USE IN THE DEVICE

BACKGROUND OF THE INVENTION

The present invention relates to a device for distributing compressed air from a source of compressed air to a plurality of apparatus that use compressed air, and also a valve for use in the device. The invention can be applied, in particular, to a pneumatic massage apparatus comprising a massage body having a plurality of airtight chambers.

Hitherto known are pneumatic massage apparatus designed to recover, maintain and promote health of persons. Each massage apparatus comprises a massage body having a plurality of airtight chambers. The massage body is attached to the arm or the leg, and compressed air is supplied into and exhausted from the chambers sequentially, thereby to massage the arm or the leg consecutively.

Most of these massage apparatus have a compressed air-distributing device each. The compressed air distributing device is designed to distribute compressed air from a compressed air source into the airtight chambers and to exhaust the compressed air from the airtight chambers. Typically, the compressed air-distributing device comprises a fixed valve housing and a rotary valve body. The fixed valve housing has an inlet passage and a plurality of distribution passages. The distribution passages are connected to a plurality of airtight chambers, respectively. Compressed air is supplied from a compressed air source to the inlet passage. The rotary valve body has a connecting groove and an exhaust port. The connecting groove is provided to connect the inlet passage to any selected one of the distribution passages. The exhaust port is provided to exhaust air from any selected one of the distribution passages.

In the compressed air-distributing device, a spring pushes the rotary valve body onto the fixed valve (housing), setting them in a mutual surface contact. Therefore, the inlet passage of the fixed valve housing always communicates with one end of the connecting groove. The rotary valve body is rotated by an electric motor, connecting the other end of the connecting groove to the distribution passages, one after another. Compressed air is thereby supplied into the airtight chambers through the respective distribution passages, inflating the airtight chambers. When the rotary valve is further rotated, it closes all distribution passages, keeping the chambers inflated. When the rotary valve is rotated still further, the distribution passages communicate with the exhaust port. The compressed air is thereby exhausted from the airtight chambers, deflating the airtight chambers. Hence, as the rotary valve is continuously rotated in the same direction, the airtight chambers are repeatedly inflated and deflated. Selected ones of the airtight chambers can be inflated and deflated by rotating the rotary valve in one direction, alternately in the forward direction and the reverse direction within a defined rotatable angle. Alternatively, commercially available solenoid valves may be used to inflate and deflate the airtight chambers over again.

The compressed air-distributing device described above has airtight chambers into which compressed air is supplied and from which the air is exhausted, by controlling the rotation of the rotary valve body. The distribution passages of the fixed valve housing are connected to the connecting groove of the rotary valve in a predetermined order. Inevitably, the airtight chambers are inflated and deflated in a fixed order. Hence, all airtight chambers cannot be inflated or deflated at the same time, though some or all of the airtight chambers can be sequentially inflated and deflated, or only one of the airtight chambers is inflated and deflated. Further, the compressed air is likely to leak, because the fixed valve housing and the rotary valve body wear at their contacting surfaces and a gap is eventually made between them.

The flow rate of the compressed air cannot be increased since the air is supplied through the connection groove with a limited cross section. Further, each airtight chamber has a limited volume.

Moreover, commercially available solenoid valves have a narrow passage and cannot supply or exhaust the compressed air into and from the airtight chamber at a high flow rate, though they can serve to inflate and deflate the airtight chambers. In addition, the commercially available solenoid valves are expensive.

BRIEF SUMMARY OF THE INVENTION

The present invention is intended to overcome the above-mentioned problems with the conventional compressed air-distributing device and the commercially available solenoid valves. One object of the present invention is to provide an inexpensive compressed air distributing valve which can supply and exhaust compressed air at a high flow rate and which excels in durability. Another object of the invention is provide an inexpensive compressed air-distributing device which can switch airtight chambers into and from which compressed air is to be supplied and exhausted, which can supply and exhaust compressed air into and from a plurality of airtight chambers at the same time, and which can supply and exhaust into and from airtight chambers at a high flow rate.

To attain the objects, a device for distributing compressed air from a compressed air source to a plurality of apparatus that use compressed air is provided according to the preset invention. The device comprises: a housing having a plurality of valve chambers, a plurality of inlet ports for connecting the valve chambers to the compressed air source, a plurality of outlet ports, each adapted to communicate with at least one of the apparatus that use compressed air, and a plurality of exhaust ports communicating with outside the device; a plurality of spherical valve bodies movably provided in the valve chambers, respectively, each for closing one inlet port and one exhaust port; a plurality of shafts extending from the valve bodies, respectively, each shaft having an end portion passing through one exhaust port and protruding from the housing; a plurality of electromagnetic actuators coupled to the end portions of the shafts, respectively, each designed to move one valve body between an air-supplying position where the valve body closes the exhaust port and connecting the inlet port and the outlet port and an air-exhausting position where the valve body closes inlet port and connecting the outlet port and the exhaust port.

In the compressed air distributing device, each of the valve bodies constitutes a three-way valve, together with one valve chamber. The three-way valves are driven by the electromagnetic actuators, respectively, to connect the outlet ports to either the inlet ports or the exhaust ports. Thus, each three-way valve is controlled independently of any other three-way valve. Hence, the device can supply and exhaust compressed air from any selected ones of the apparatuses at the same time.

Since the valve bodies are spherical, they occupy only a small space in the respective valve chambers. A large air passage is therefore provided in each valve chamber. The three-way valves are extremely simple in structure and can be inexpensive. Incorporating inexpensive valves, the compressed air-distributing device can be manufactured at low cost.

It is desired that each of the electromagnetic actuators have a movable member, an electromagnet for moving the movable member and a spring biasing the movable member. Also is it desired that each of the valve bodies remain at one of the air-supplying position and air-exhausting position while no electric current is supplied to the electromagnet.

Further, it is desired that the device should further comprise a header extending parallel to the housing and adapted to be connected to the compressed air source, and that the inlet ports should be connected by the header to the compressed air source.

Furthermore, it is desired that the end portions of the shafts be pivotally coupled to the movable members of the electromagnetic actuators, respectively. If the end portions are so coupled to the movable members, each valve body can reliably close the inlet port and the exhaust port even if its axis is not aligned with that of the inlet port or exhaust port.

It is also desired that each valve body have a surface portion made of elastic material. If the valve body has such a surface portion, it will provide an appropriate sealing surface.

Furthermore, a valve is provided according to the invention, for use in a device designed to distribute compressed air from a compressed air source to a plurality of apparatus that use compressed air. The valve comprises: a housing having a valve chamber, a inlet port for connecting the valve chamber to the compressed air source, an outlet port adapted to communicate with at least one of the apparatus that use compressed air, and an exhaust port communicating with outside the device; a spherical valve body movably provided in the valve chamber, each for closing one inlet port and one exhaust port; a shaft extending from the valve body and having an end portion passing through the exhaust port and protruding from the housing; an electromagnetic actuator coupled to the end portion of the shaft and designed to move the valve body between an air supplying position where the valve body closes the exhaust port and connecting the inlet port and the outlet port and an air-exhausting position where the valve body closes inlet port and connecting the outlet port and the exhaust port.

It is desired that the electromagnetic actuator have a movable member, an electromagnet for moving the movable member and a spring biasing the movable member. Also is it desired that the valve body remain at one of the air-supplying position and air-exhausting position while no electric current is supplied to the electromagnet.

Furthermore, it is desired that the end portion of the shaft be pivotally coupled to the movable member of the electromagnetic actuator. If the end portion is so coupled to the movable member, the valve body can reliably close the inlet port and the exhaust port even if its axis is not aligned with that of the inlet port or exhaust port.

It is also desired that the valve body have a surface layer made of elastic material. If the valve body has such a surface layer, it will have an appropriate sealing surface.

Additional objects and advantages of the invention will be set forth in the description which follows, and in part will be obvious from the description, or may be learned by practice of the invention. The object and advantages of the invention may be realized and obtained by means of the instrumentalities and combinations particularly pointed out hereinafter.

BRIEF DESCRIPTION OF THE SEVERAL VIEWS OF THE DRAWINGS

The accompanying drawings, which are incorporated in and constitute a part of the specification, illustrate presently preferred embodiments of the invention, and together with the general description given above and the detailed description of the preferred embodiments given below, serve to explain the principles of the invention.

DESCRIPTION OF THE INVENTION

A preferred embodiment of the present invention will be described, with reference to the accompanying drawings.

Figure 1:
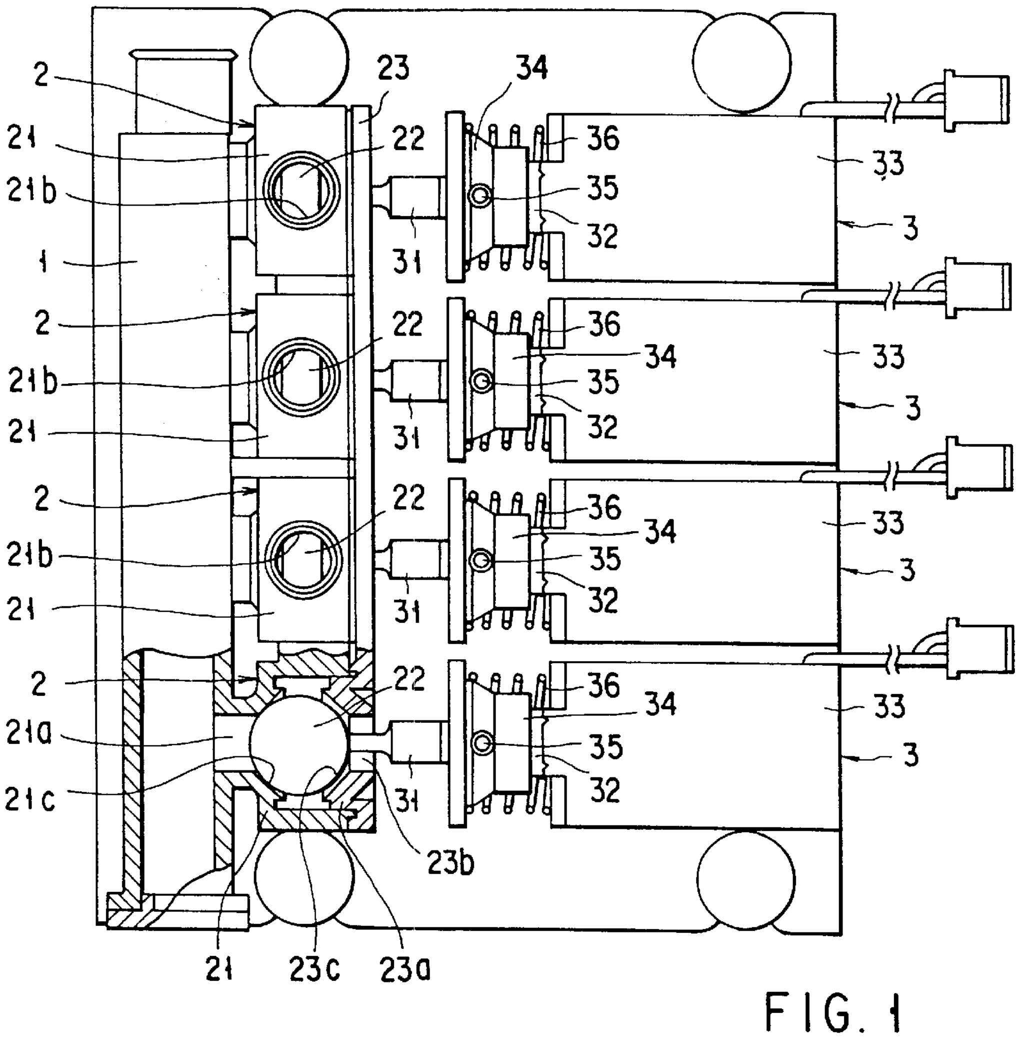
FIG. 1 is a plan view of a compressed air-distributing device according to the present invention.
Figure 3:
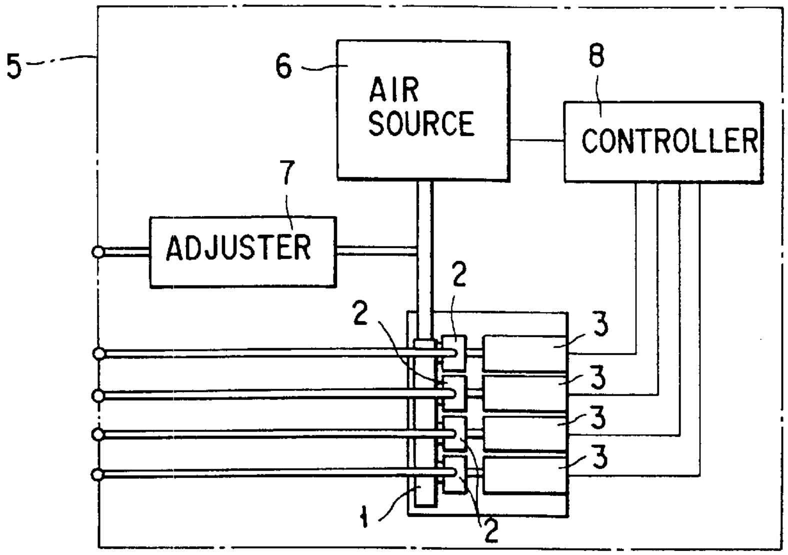
FIG. 3 is a schematic diagram showing the air circuit and electric circuit which are provided in a massage apparatus comprising the compressed air distributing device.

As shown in FIG. 1, the compressed air-distributing device according to the invention comprises a hollow cylindrical header 1, a plurality of control valves, or switching valves 2, and a plurality of solenoid sections 3. The header 1 is connected to a compressed air source 6 (FIG. 3). The switching valves 2 are arranged side by side, along the header 1. Each control valve 1 incorporates a valve body 22. The solenoid sections 3, or electromagnetic actuators, are provided to actuate the valve bodies 22 of the switching valves 2, respectively. The number of switching valves 2 is determined in accordance with the number of passages through which compressed air should be supplied. Four switching valves 2 are provided in the compressed air-distributing device shown in FIG. 1.

Figure 2:
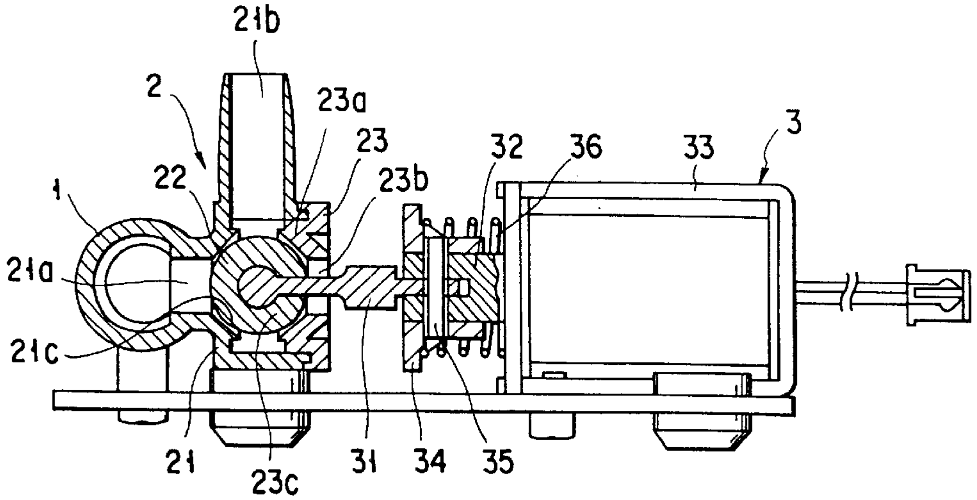
FIG. 2 is a sectional view of the compressed air-distributing device shown in FIG. 1.

As shown in FIG. 2, each switching valve 2 comprises a valve housing or box 21, a valve body 22 and a plate-shaped cover 23. The valve box 21 is made of resin and formed integral with the header 1, which is made of resin. The valve body 22 is spherical, made of elastic material (e.g., silicone rubber, chloroprene rubber, ethylene-propylene rubber, or the like). The cover 23 is made of resin and provided at the open end of the valve box 21. The valve box 21 defines four valve chambers. Each of the valve chambers communicates with an inlet port 21*a* in the side close to the header 1 and an outlet port 21*b* in the upper part. The outlet port 21*b* communicates with the passage provided in the header 1. The outlet port 21*b* can communicate with an airtight chamber 11 (FIG. 5) provided in a massage body 10 (FIG. 5). The valve box 21 further has a seat surface 21*c* at the inner periphery of the inlet port 21*a*. The seat surface 21*c* has a conical or spherical inner surface on which the valve body abuts. The cover 23, which closes the open end of the valve box 21 and which opposes the inlet port 21*a* has a valve seat 23*a*. The valve seat 23*a* defines an exhaust port 23*b* and a seat surface 23*c*. The seat surface 23*c* is provided on the inner periphery of the exhaust port 23*b*. The surface 23*c* is either a conical one or a spherical one.

Each solenoid section 3 has a shaft 31. The shaft 31 is connected at one end to the valve body 22 of the switching valve 2 associated with the solenoid section 3. The valve body 22 is arranged in the valve box 21, and the cover 23 is fastened to the open end of the valve box 21. The other end of the shaft 31 extends outwardly through the exhaust port 23*b* made in the cover 23. Thus, the valve body 22 is coupled to the solenoid section 3 through the shaft 31. The valve body 22 may have a surface layer made of elastic material.

Each solenoid section 3 comprises a shaft 31, a movable member 32, an electromagnet case 33, a flange 34, a pin 35, and a spring 36. The shaft 31 is connected to the valve body 22 at one end and to the movable member 32 at the other end projecting through the exhaust port 23*b*. The electromagnet case 33 contains the movable member 32 and a coil. The flange 34 is fastened to the distal end of the movable member 32. The pin 35 fastens the shaft 31 and the flange 34 to the distal end of the movable member 32. The spring 36 is wound around the movable member 32 and interposed between the case 33 and the flange 34. Usually, no electric current flows through the coil, and the movable member 32 is located near the switching valve 2 by virtue of the force of the spring 36. In this condition, the valve body 22 at the distal end of the shaft coupled to the movable member 32 is located in an air-exhausting position. That is, it abuts on the seat surface 21*c*, closing the inlet port 21*a* and connecting the outlet port 21*b* to the exhaust port 23*b*. When an electric current flows through the coil, the coil generates an electromagnetic force, which pulls the movable member 32 into the electromagnet case 33 against the force of the spring 36. The valve body 22 attached to the distal end of the shaft 31 coupled to the movable member 32 is thereby moved away from the seat surface 21*c* to an air-supplying position. At the air-supplying position, the valve body 22 abuts on the seat surface 23*c* of the exhaust port 23*b*. As a result, the exhaust port 23*b* is closed, and the input port 21*a* and outlet port 21*b* are connected.

As shown in FIG. 3, the compressed air-distributing device is incorporated in the body 5 of a massage apparatus, together with a compressed air source 6, a pressure-adjusting mechanism 7 and a control section 8. The compressed air source 6 is, for example, a compressor. The control section 8 is provided for controlling the compressed air-distributing device and the compressed air source 6. The pressure-adjusting mechanism 7 is connected to an air-supplying pipe, which connects the compressed air source 6 to the header 1 of the compressed air distributing device. The output ports 21*b* of the switching valves 2 are connected to the air inlet port of the body 5 of the massage apparatus. The exhaust ports 23*b* of the switching valves 2 are connected to an exhaust pipe which communicates with the outside of the body of the massage apparatus. The solenoid sections 3 and compressed air source 6 are electrically connected to the control section 8.

It will be described how the compressed air distributing device according to the invention operates in the pneumatic apparatus shown in FIG. 4.

Figure 4:
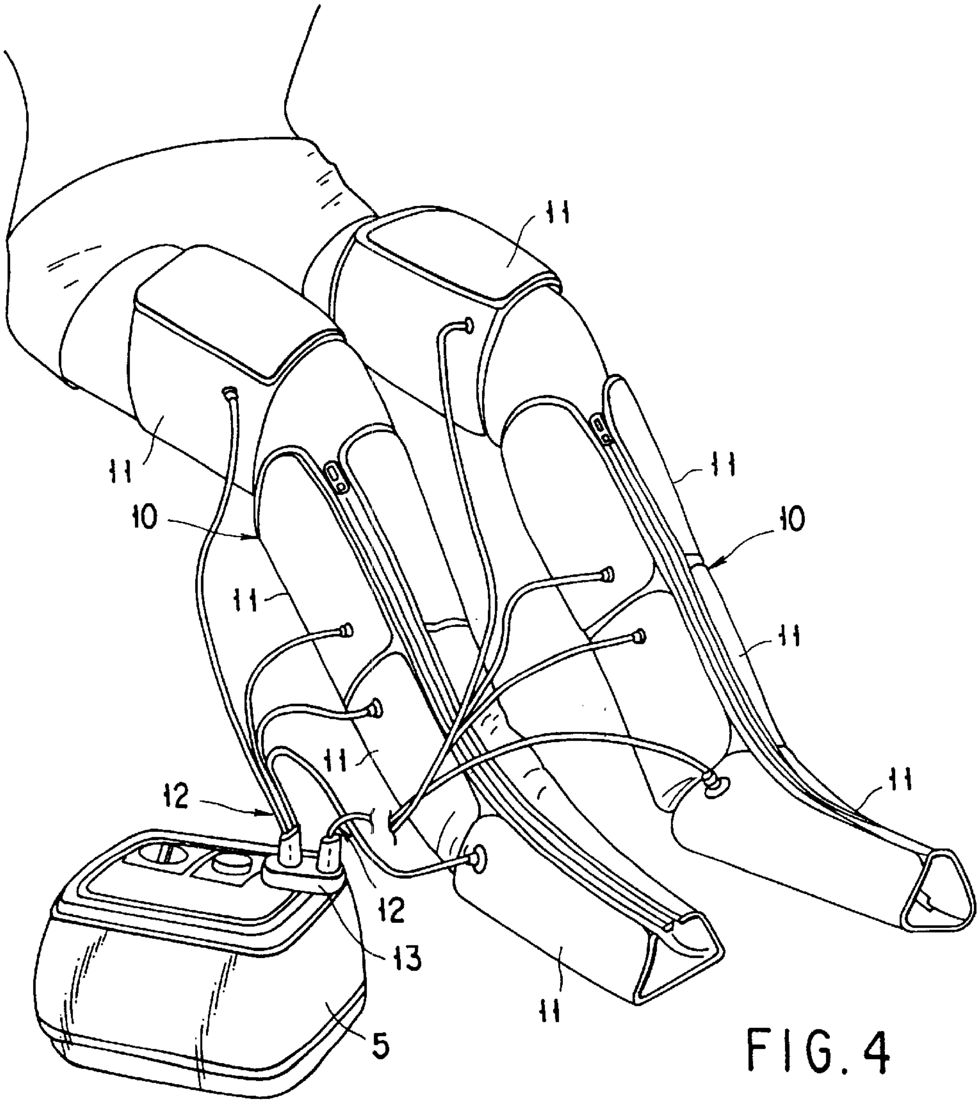
FIG. 4 is a perspective view of the massage apparatus shown in FIG. 3.

As shown in FIG. 4, air hoses 12 are connected at one end to the body 5 by an adapter 13. The adapter 13 connects the outlet ports 21*b* of the switching valves 2 to the airtight chambers 11 provided in two massage bodies 10, respectively. The air houses 12 are connected at the other end to the airtight chambers 11, respectively. To massage only one leg of the user, it suffices to connect the air hoses 12 at said one end, directly to the body of the massage apparatus.

The massage bodies 10 are wrapped around the legs, respectively. The power switch to the body 5 is closed, and the switches provided on the body 5 of the massage apparatus are turned on, whereby the massage apparatus starts massaging the legs.

More specifically, the compressed air source 6 starts operating, supplying compressed air, and the control section 8 starts turning on and off the solenoid sections 3 in one of three programmed modes. The number of programmed modes is not limited to three. The control section 8 may turn on and off the solenoid sections 3 in more or less modes.

In the first programmed mode, all solenoid sections 3 are turned on at the same time. Upon lapse of a predetermined time, all solenoid sections 3 are turned off at the same time, equalizing the pressures in all airtight chambers 11. Next, the control section 8 turns on and off the first to fourth solenoid sections 3 one after another. More precisely, the first solenoid section 3 first opens the switching valves 2 communicating with the most distal airtight chamber 11 and closes the same upon lapse of a prescribed time. Then, the second solenoid section 3 opens the switching valves 2 communicating with the second most distal airtight chamber 11 and closes the same upon lapse of the prescribed time. Next, the third solenoid section 3 opens the switching valves 2 communicating with the third most distal airtight chamber 11 and closes the same upon lapse of the prescribed time. Finally, the fourth solenoid section 3 opens the switching valves 2 communicating with the most proximal airtight chamber 11 and closes the same upon lapse of the prescribed time. The control section 8 turns on and off the fourth solenoid sections 3 repeatedly in this specific sequence, whereby the massage apparatus massages the leg repeatedly, each time from the distal end to the proximal end.

In the second programmed mode, all solenoid sections 3 are turned on at the same time and turned off simultaneously upon lapse of a predetermined time, equalizing the pressures in all airtight chambers 11, as in the first programmed mode. Next, the control section 8 turns on the first to fourth solenoid sections 3 one after another. As a result, the first to fourth switching valves 2 are opened one after another, in order mentioned. The massage apparatus therefore massages the leg, from the distal end to the proximal end. Upon lapse of a prescribed time, all solenoid sections 3 are turned off. The control section 8 turns on and off the fourth solenoid sections 3 repeatedly in this particular sequence. Hence, the massage apparatus massages the leg repeatedly, each time first massaging the leg from the distal end to the proximal end and stopping the application of a pressure to all parts of the leg upon lapse of the prescribed time.

In the third programmed mode, all solenoid sections 3 are repeatedly turned on and off simultaneously at regular intervals, until a preset time expires. As a result, the massage apparatus repeatedly applies a pressure to all parts of the leg and stops applying the pressure thereto.

When the control section 8 turns on any solenoid section 3, an electric current flows through the coil in the electromagnet case 33 of the solenoid section 3. The movable member 32 is pulled into the case 33 against the force of the spring 36. The valve body 22 is moved from the seat surface 21*c* of the input port 21*a*, because the valve body 22 is attached to the distal end of the shaft 31 coupled to the movable member 32. The valve body 22 abuts on the seat surface 23*c* of the exhaust port 23*b*, closing the exhaust port 23*b* and connecting the input port 21*a* and outlet port 21*b*. As a result, the compressed air supplied from the source 6 flows from the inlet port 21*b* into the airtight chambers 11 through the adapter 13 and the air hoses 12. The airtight chambers 11 associated with the solenoid section 3 are thereby inflated. At this time, the pressure-adjusting mechanism 7 connected to the compressed air source 6 releases a part of the compressed air outside, preventing the pressure in the airtight chambers 11 from increasing excessively. When the control section 8 turns off any solenoid section 3, the electric current stops flowing through the coil. The movable member 32 is moved to the switching valve 2 due to the force of the spring 36. The valve 2 body 22 at the distal end of the shaft 31 coupled to the movable member 32 abuts on the seat surface 21*c* of the input port 21*a*. The inlet port 21*a* is thereby closed, preventing the compressed air from flowing through the inlet port 21*a* into the switching valve 2. Furthermore, the outlet port and the exhaust port 23*b* are connected. The compressed air is exhausted through the exhaust port 23*b* from the airtight chambers 11 connected to the outlet port 21*b*. The airtight chambers 11 are thereby deflated.

As has been described above, the solenoid sections 3 have been turned on and off repeatedly, each time for a prescribed time, inflating and deflating the airtight chambers 11. Then, the compressed air source 6 is stopped, and all solenoid sections 3 are turned off. As a result, all airtight chambers 11 deflate. Thus, the massage apparatus stops operating.

In each solenoid section 3, the shaft 31 coupled to the distal end of the movable member 32 can oscillate around the pin 35 and can vertically move a little. The center of the valve body 22 is therefore automatically set at the center of curvature of the seat surface 21*c* or that of the seat surface 23*c*, even if the locus of the body 22 does not pass the centers of curvature of the seat surfaces 21*c* and 23*c*. Hence, the valve body 22 completely closes the inlet port 21*a*, the outlet port 21*b* and the exhaust port 23*b*. Moreover,since the valve body 22 is made of elastic material, it reliably closes the ports 21*a*, 21*b* and 23*b*, preventing leakage of the compressed air.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalent.

What is claimed is:

1. A device for distributing compressed air from a compressed air source to a plurality of apparatus that use compresses air, said device comprising:

a housing having a plurality of valve chambers, a plurality of inlet ports for connecting the valve chambers to the compressed air source, each adapted to communicate with at least one of the apparatus that use compressed air, and a plurality of exhaust ports communicating with outside the device, each inlet port opposing the corresponding exhaust port, and the inlet ports and exhaust ports each having one of a spherical valve seat and a conical valve seat that has a diameter gradually increasing toward the valve chamber;

a plurality of spherical valve bodies movably provided in the valve chambers, respectively, each of said spherical valve bodies (i) having a surface layer made of elastic material and (ii) to be placed in the valve seat of one of the inlet port and the exhaust port to close one of the inlet port and the exhaust port;

a plurality of shafts extending from the valve bodies, respectively, each shaft having an end portion passing through one exhaust port and protruding from the housing; and a plurality of electromagnetic actuators pivotally coupled to the end portions of the shafts, respectively, each designed to move one valve body between an air-supplying position where the valve body closes the exhaust port and connecting the inlet port and the outlet port and an air-exhausting position where the valve body closes the inlet port and connecting the outlet port and the exhaust port, said surface layer of said elastic material covering substantially the entire outer surface of said spherical body so as to fully engage and seal the valve seat of the inlet port in the air-exhausting position and to fully engage and seal the valve seat of the exhaust port in the air-supplying position.

2. A device according to claim 1, wherein each of the electromagnetic actuators has a movable member, an electromagnet for moving the movable member and a spring biasing the movable member, and each of the valve bodies remains at one of the air-supplying position and air-exhausting position while no electric current is supplied to the electromagnet.

3. A device according to claim 1, further comprising a header extending parallel to the housing and adapted to be connected to the compressed air source, for connecting the input ports to the compressed air source.

4. A device according to claim 2, wherein the end portions of the shafts are pivotally coupled to the movable members of the electromagnetic actuators, respectively.

5. A valve for use in a device designed to distribute compressed air from a compressed air source to a plurality of apparatus that use compressed air, said valve comprising:

a housing having a valve chamber, an inlet port for connecting the valve chamber to the compressed air source, an outlet port adapted to communicate with at least one of the apparatus that use compressed air, and an exhaust port communicating with outside the device, the inlet port opposing said exhaust port, and the inlet port and exhaust port each having one of a spherical valve seat and a conical valve seat that has a diameter gradually increasing toward the valve chamber;

a spherical valve body having a surface layer made of elastic material and movably provided in the valve chamber, to be placed in the valve seat of one of the inlet port and the exhaust port to close one of the inlet port and the exhaust port;

a shaft extending from the valve body and having an end portion passing through the exhaust port and protruding from the housing; and an electromagnetic actuator pivotally coupled to the end portion of the shaft and designed to move the valve body between an air-supplying position where the valve body closes the exhaust port and connecting the inlet port and the outlet port and an air-exhausting position where the valve body closes the inlet port and connecting the outlet port and the exhaust port, said surface layer of said elastic material covering substantially the entire outer surface of said spherical body so as to fully engage and seal the valve seat of the inlet port in the air-exhausting position and to fully engage and seal the valve seat of the exhaust port in the air-supplying position.

6. A device according to claim 5, wherein the electromagnetic actuator has a movable member, an electromagnet for moving the movable member and a spring biasing the movable member, and the valve body remains at one of the air-supplying position and air exhausting position while no electric current is supplied to the electromagnet.

7. A device according to claim 6, wherein the end portion of the shaft is pivotally coupled to the movable member of the electromagnetic actuator.

* * * * *